United States Patent [19]

Erskine et al.

[11] Patent Number: 5,304,136
[45] Date of Patent: Apr. 19, 1994

[54] NEEDLE SHEATH

[75] Inventors: Timothy J. Erskine, Salt Lake City; Christopher P. Steinman, Sandy, both of Utah

[73] Assignee: Becton, Dickinson and Company, Franklin Lakes, N.J.

[21] Appl. No.: 832,241

[22] Filed: Feb. 7, 1992

[51] Int. Cl.$^5$ .............................................. A61M 5/00
[52] U.S. Cl. .................................... 604/110; 604/164; 604/263
[58] Field of Search ............... 604/110, 192, 194, 198, 604/199, 162, 263, 195, 197; 128/763-765; 206/364, 365

[56] References Cited

U.S. PATENT DOCUMENTS

| | | | |
|---|---|---|---|
| 4,762,516 | 8/1988 | Luther et al. | 604/110 |
| 4,927,415 | 5/1990 | Brodsky | 604/198 |
| 4,994,728 | 7/1990 | Carrell et al. | 604/110 |
| 4,998,924 | 3/1991 | Ranford | 604/110 |
| 5,061,246 | 10/1991 | Anapliotis | 604/192 |
| 5,135,502 | 8/1992 | Koenig. Jr. et al. | 604/110 |
| 5,137,515 | 8/1992 | Hogan | 604/110 |
| 5,147,326 | 9/1992 | Talonn et al. | 604/110 |

FOREIGN PATENT DOCUMENTS 0314470  10/1988  European Pat. Off. .

Primary Examiner—C. Fred Rosenbaum
Assistant Examiner—Chalin Smith
Attorney, Agent, or Firm—Michael G. Schwarz

[57] ABSTRACT

A needle shielding device in which, after use, a needle is confined in a chamber having a first hole through which the needle can enter the chamber. The needle is drawn into the chamber through the hole. The chamber is made up of telescopic members. The needle strikes the rear wall of the chamber causing the telescopic members to telescope apart. Once in the chamber, the needle will not readily escape through the first hole.

22 Claims, 3 Drawing Sheets

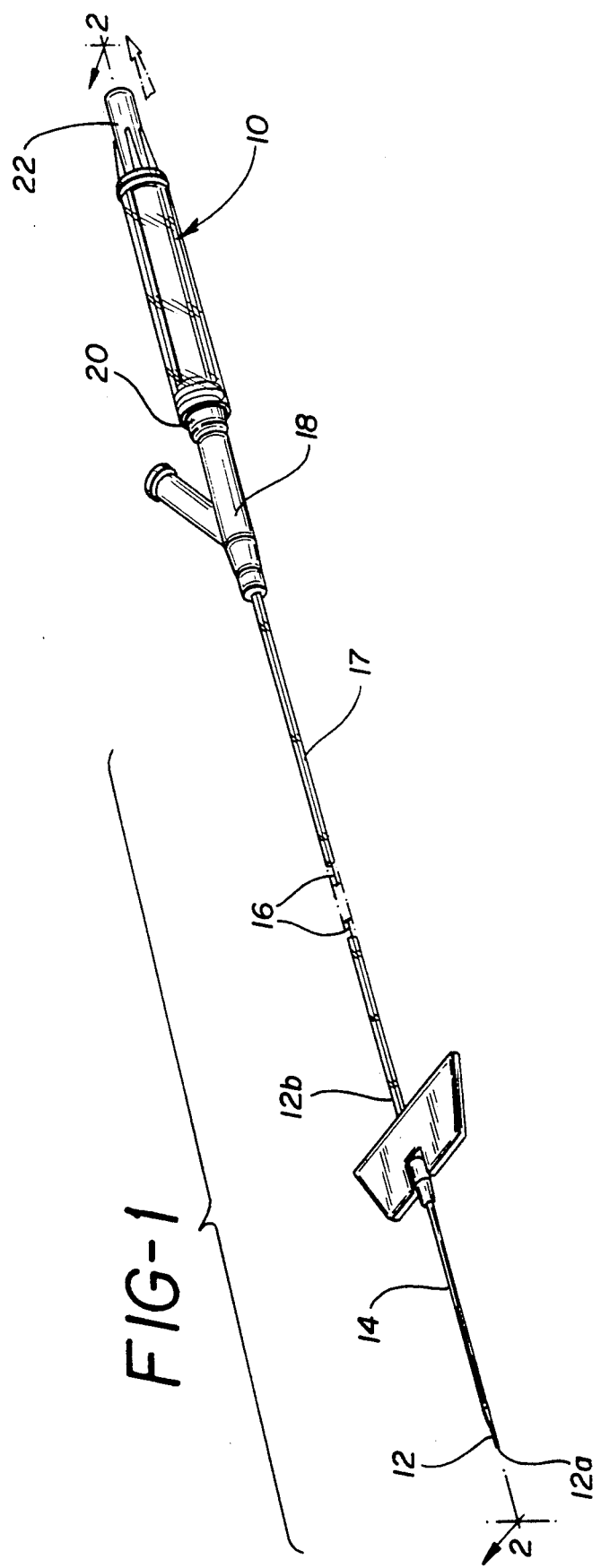

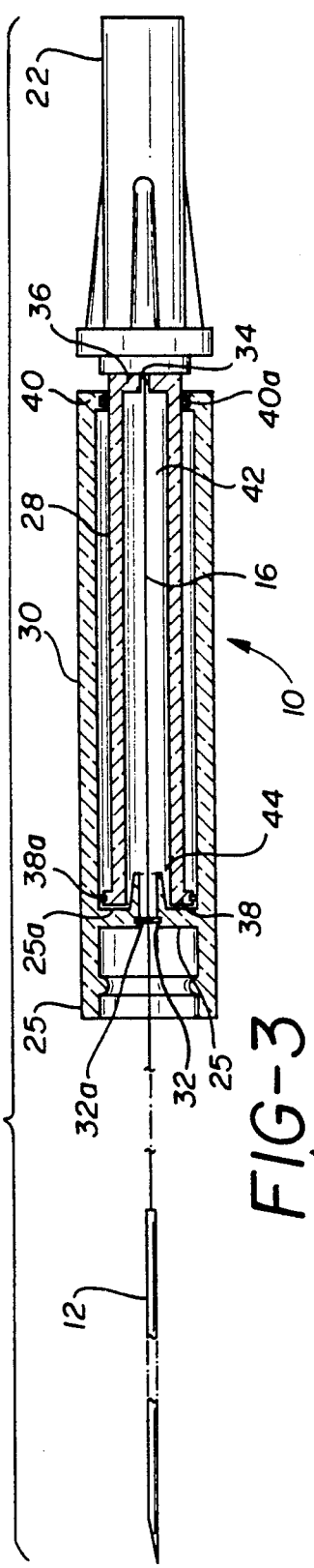
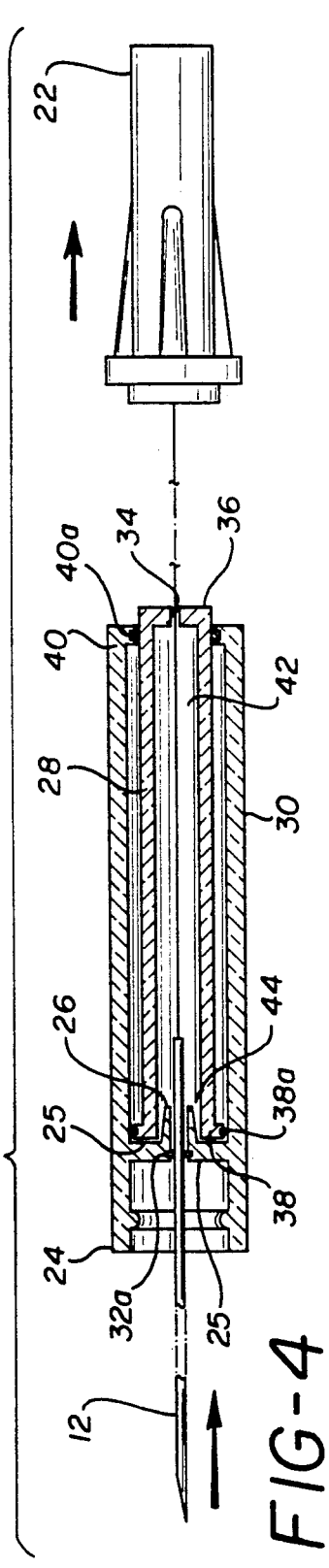
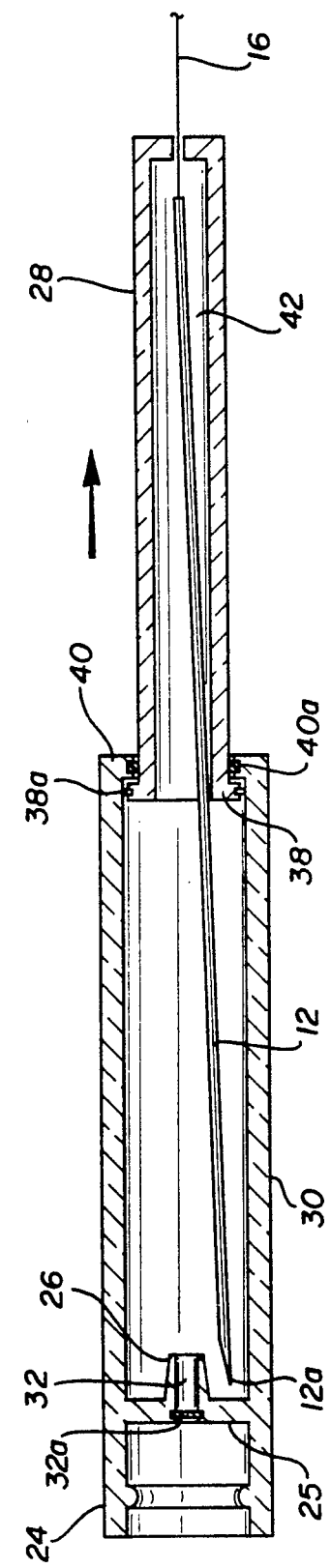

NEEDLE SHEATH

BACKGROUND OF THE INVENTION

The present invention relates to the shielding of needles used for the placement of catheters into the bodies of animals or human animals.

There is a need for the shielding of sharp instruments such as catheter introducing needles used in the medical field. Shielding is needed to minimize the risk of needle sticks by needles which might be contaminated with disease causing viruses and bacteria.

SUMMARY OF THE INVENTION

This invention for shielding a needle comprises a hollow chamber into which the needle is drawn following its contamination with a fluid such as blood. It is typically used in conjunction with a catheter introduction device. An example of such a typical catheter introduction device is the Intima TM intravenous catheter placement set produced by Becton, Dickinson and Company of Franklin Lakes, N.J. In this device, the needle is surrounded by a concentric intravenous catheter. This catheter is typically connected to a flexible tube through which medications may be introduced. The distal end of the needle is attached to a thin wire or stylet and the needle may be drawn out of the catheter, through the flexible tube and into a chamber by pulling the stylet. The needle and stylet are then discarded. The diameter of the stylet is smaller than that of the needle. The invention may be used in any similar application involving a needle having a narrower pulling means attached to it.

The chamber is made of telescopically interconnected members and has front and rear walls In the preferred embodiment the front and rear walls have axial holes. The front hole is dimensioned with minimal clearance between hole and needle, so the needle will just slip through the hole longitudinally but nothing larger will slip through it. At the opposite end of the chamber, in the back wall, is another axial hole through which the stylet can pass. This back hole is dimensioned with minimal clearance between the hole and the stylet so that only the stylet, but not the needle will pass through it. Once the needle has passed through the front hole and into the chamber, it will fall or be forced towards a side wall of the chamber. The resiliency of the stylet will cause the needle to move out of axial alignment with the front hole.

Inside the chamber the front hole may be provided with a surrounding collar or rim. The collar or rim provides an obstacle to prevent the needle from re-entering the hole and thus leaving the chamber and posing a risk of a needle stick. The chamber is dimensioned so that the needle will just fit into it lengthwise. Thus, the geometry of the inside of the chamber also makes it difficult for the needle to be repositioned relative to the front hole in order to exit the chamber. The chamber is constructed in a telescopic fashion so that it is compact during insertion of the needle into a patient, but expands to be large enough to accommodate the needle when the needle is withdrawn. The front end of the chamber may also have a variety of configurations to accommodate various connectors so that it can simply be connected to existing catheters and catheter introducers. Luer connectors, friction connectors and the like may be used.

Other objects, features and advantages of the invention will become apparent from the following drawings, description and claims.

BRIEF DESCRIPTION OF THE DRAWINGS

FIG. 1 is a perspective view of the preferred embodiment of the needle sheath shown in its inactive state connected to a catheter set;

FIG. 2 is a cross sectional view of the preferred embodiment of the needle sheath in its inactive state taken through section 2—2 of FIG. 1;

FIG. 3 is a cross sectional view of the preferred embodiment of the needle sheath during the process of drawing the needle into the sheath;

FIG. 4 is a cross sectional view of the preferred embodiment of the needle sheath once the needle has been fully drawn into it;

DETAILED DESCRIPTION

Figure 5:
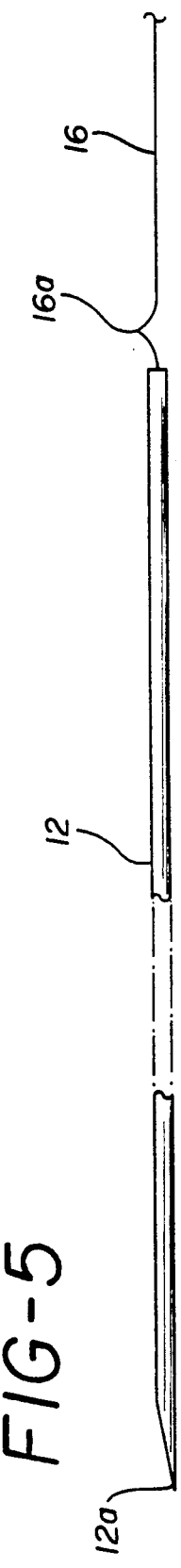
FIG. 5 is a side view of an alternative embodiment of the needle and stylet.
Figure 6:
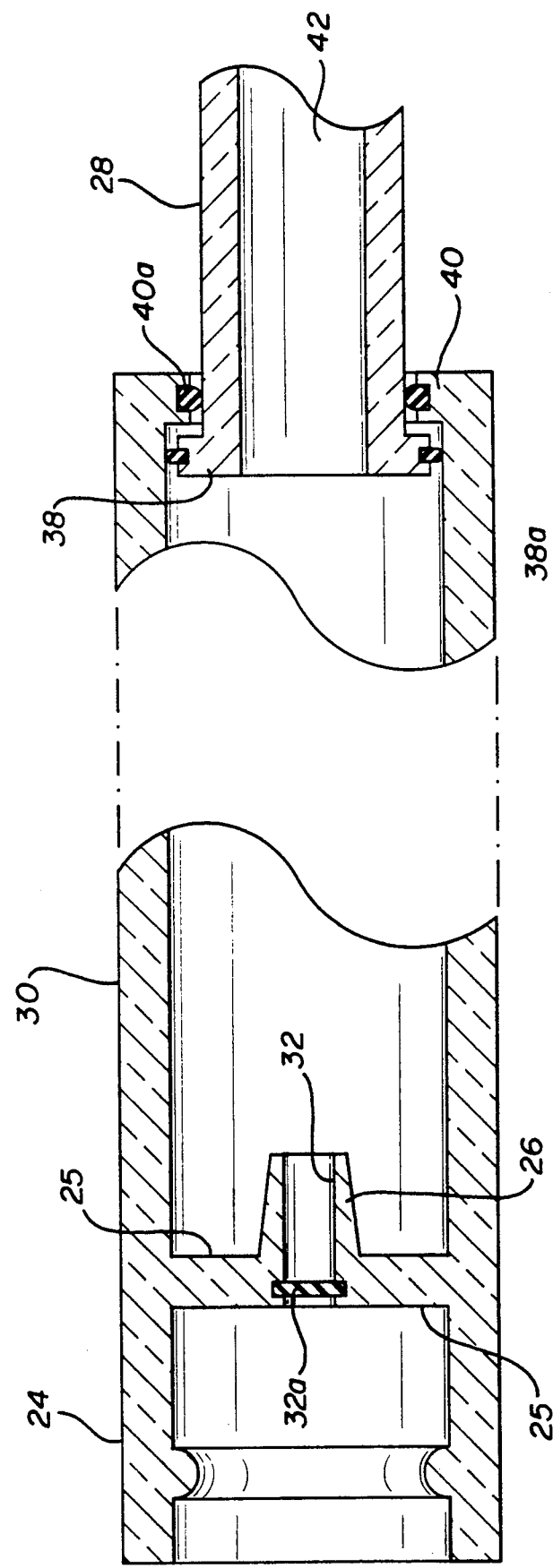
FIG. 6 is a detailed cross sectional view of the preferred embodiment of the needle sheath after the needle has been fully drawn into it.

FIG. 1 shows the needle sheath 10 used in conjunction with a catheter placement set in a typical configuration comprising an over-the needle catheter 14, a catheter introducer needle 12 having distal end 12a and proximal end 12b, a stylet 16 attached to the proximal end 12b of needle 12, a connector 18 having connector hub 20 and a stylet hub 22.

The process of introducing a catheter into a vessel using the above described catheter placement set is well known. Typically the introducer needle 12 pierces the skin and the vessel into which catheter 14 is to be introduced and catheter 14 is inserted into the vessel. Once catheter 14 has been satisfactorily located in the vessel, needle 12 is withdrawn by pulling stylet hub 22 which is attached to stylet 16.

Using the present invention attached to hub 20, the continued pulling of stylet hub 22 results in needle 12 being drawn through tube 17 and into needle sheath 10. Needle sheath 10 is then removed and connector hub 20 may be used to introduce medications, I.V. tubing or the like into the catheter in a well known way. For example, hub 20 may have a silicone septum or PRN into which a needle may be inserted or a luer connector to which various devices may be connected.

FIG. 2 shows the preferred embodiment of needle sheath 10 in cross-section, prior to the introduction of needle 12 into needle sheath 10. The embodiment shown in FIG. 2-4 is the preferred embodiment having two telescoping cylinders 28 and 30. The use of telescoping cylinders 28 and 30 facilitates compactness of the device. More than two telescopic cylinders may also be used for greater compactness and greater expanded size.

While telescoping cylinders 28 and 30 have circular cross-sections, cylinders 28 and 30 can have any cross section which can confine a needle such as square, triangular, hexagonal or elliptical cross-sections. Outer cylinder 30 comprises connector 24, shown as a female connector used to connect sheath 10 to hub 20. Several different types of connector such as male or female luer connectors, well known in the art, may be used to attach needle sheath 10 to connector 18. A simple snap fitting is shown for connection of the sheath to a PRN well known in the art.

Inner cylinder 28 fits concentrically inside outer cylinder 30. Cylinders 28 and 30 thus form chamber 42. Cylinder 30 has first end wall 25 which has orifice 32 located at its center. Orifice 32 is dimensioned to allow needle 12 to slide through it and into chamber 42 as shown in FIG. 3. Orifice 32 is provided with a seal 32a such as a silicone septum or equivalent which prevents fluid from entering chamber 42 and also prevents needle 12 from exiting orifice 32 once fully entered chamber 42 as described herein. On the inside 25a of cylinder wall 25, surrounding orifice 32 is collar 26. Collar 26 preferably has a generally conical shape.

At the open end 44 of cylinder 28, on the outer wall of cylinder 28 is an outwardly facing lip 38. Lip 38 is provided with a sealing ring 38a to prevent liquid from escaping from chamber 42. Outer cylinder 30 has a lip 40 at its end opposite wall 25 which is inwardly facing to complement lip 38. Lip 40 may also be provided with a sealing ring 40a in addition to and similar to sealing ring 38a. The orientations of the lips are interchangeable. Likewise, cylinder 30 may fit inside cylinder 28 and vice versa.

Cylinder 28 has a back wall 36. Back wall 36 has orifice 34 at its center point. Orifice 34 is dimensioned such that there is sufficient clearance for stylet 16 to slip through it longitudinally, but such that it is too small to allow the larger diametered needle 12 to pass through it. Orifice 34 may also be provided with seal 34a such as a silicone septum or equivalent which prevents fluid from leaking out of orifice 34. The diameters of orifices 32 and 34 will be dictated by the particular needle and stylet with which the needle sheath is used. Typically in a 24-gauge catheter application stylet 16 will have a diameter of 0.2 mm. Needle 12 will have an outside diameter of 0.47 mm. Therefore orifice 32 will have a diameter of 0.5 mm and orifice 34 will have a diameter of 0.25 mm.

FIG. 3 shows needle 12 entering into chamber 42. Once catheter 14 has been satisfactorily placed, stylet 16 is pulled by means of hub 22 through orifice 34 so that needle 12 is withdrawn from catheter 14 and moves longitudinally in the direction of orifice 34. When the proximal end of needle 12 reaches orifice 34, it will strike rear wall 36 and will be unable to fit through orifice 34. Continued pulling of stylet 16 results in the telescopic expansion of chamber 42 because cylinder 28 will be drawn by the force of needle 12 being pulled against back wall 36. The telescopic expansion of chamber 42 will continue until lips 38 and 40 meet. At or before that point, needle 12 will be inside chamber 42 as shown in FIG. 4. Cylinders 28 and 30 will not be able to collapse together because of the presence of needle 12.

Needle 12 will fall towards the wall of cylinder 30 due to gravity. Stylet 16 may be provided with a slight kink 16a adjacent needle 12 as shown in FIG. 5. Kink 16a though not preferred tends to force the needle towards the wall of cylinder 30, thus preventing it from exiting orifice 32. It will also be very difficult or impossible for needle 12 to re-enter orifice 32 because of the presence of collar 26 as shown in FIG. 4. If seal 32a is present, it will be practically impossible for needle 12 to exit orifice 32. The probability of needle 12 exiting orifice 32 is thus very small. Needle 12 is therefore confined to sheath 10 and will not present a stick hazard. To make it difficult to use stylet 16 to reposition needle 12 in line with orifice 32, cylinders 28 and 32 are preferably of an opaque material.

Once needle 12 is located in sheath 10, sheath 10 and stylet 16 may be removed from connector 18 and discarded.

While the invention described herein constitutes a preferred embodiment of the invention, it is to be understood that the invention is not limited to the precise form described herein. Changes may be made without departing from the scope of the invention which is to be determined by the scope of the appended claims and their equivalents.

We claim:

1. An apparatus for shielding a needle comprising: containment means for containing said needle, wherein said containment means comprises:
    a first telescopic member comprising a front wall, said front wall having a first orifice;
    a second telescopic member having a rear wall such that said first telescopic member and said second telescopic member form a chamber to accommodate a needle and such that said first orifice is dimensioned to permit said needle to enter said chamber through said first orifice, wherein said rear wall has a second orifice dimensioned such that said needle cannot pass through said second orifice.

2. The apparatus of claim 1 further comprising means to connect said apparatus to catheter introduction means so that said needle can be moved from said catheter introducing means into said chamber.

3. The apparatus of claim 1 wherein at least one of said telescopic members is at least partially opaque.

4. The apparatus of claim 1 further comprising sealing means for penetrably sealing said first orifice.

5. The apparatus of claim 1 wherein said front wall is provided with collar means surrounding said front orifice.

6. The apparatus of claim 5 wherein said collar means is generally conical.

7. The apparatus of claim 1 further comprising pulling means for pulling said needle through said first orifice towards said rear wall.

8. The apparatus of claim 7 wherein said pulling means comprises stylet means attached to said needle.

9. The apparatus of claim 8 wherein said stylet means is provided with a kink adjacent said needle.

10. The apparatus of claim 7 wherein said pulling means has a smaller diameter than said needle and said second orifice is dimensioned to allow said pulling means but not said needle to pass therethrough.

11. The apparatus of claim 7 wherein said first telescopic member and said second telescopic member telescope apart when said needle has entered said chamber.

12. The apparatus of claim 7 wherein said first telescopic member and said second telescopic member telescope apart when said needle strikes said rear wall.

13. An apparatus for shielding a catheter introducing needle comprising:
    a cylinder comprising first and second telescopic cylinders, the first cylinder having a front wall and the second cylinder having a back wall;
    a needle;
    pulling means attached to said needle; and
    means for connecting said cylinder to a fitting,
    wherein said front wall is provided with an orifice through which said needle may enter said cylinder longitudinally and said back wall is provided with an orifice through which said stylet may pass longitudinally, but through which said needle cannot pass.

14. The apparatus of claim 13 wherein said cylinder is at least partially opaque.

15. The apparatus of claim 13 wherein said cylinders telescope apart when said needle has entered said cylinder.

16. The apparatus of claim 13 further comprising sealing means for penetrably sealing said orifice.

17. An apparatus for shielding a catheter introducing needle comprising:
   a first cylinder having a front wall and an open end;
   a second cylinder having a rear wall and an open end, said front wall having a first orifice and said rear wall having a second orifice;
   a needle;
   stylet means connected to said needle for drawing said needle through said first orifice towards said rear wall, wherein said stylet has a diameter less than that of said needle;
   wherein said first orifice is dimensioned to allow said needle to pass longitudinally therethrough and said second orifice is dimensioned to permit said stylet but not said needle to pass longitudinally therethrough and further wherein said first cylinder and said second cylinder are telescopically interconnected.

18. The apparatus of claim 17 wherein at least one of said cylinders is at least partially opaque.

19. The apparatus of claim 7 wherein said first and second cylinders telescope apart when said needle strikes said rear wall.

20. The apparatus of claim 17 wherein said stylet means is provided with a kink adjacent said needle.

21. The apparatus of claim 17 wherein said front wall comprises collar means surrounding said first orifice inside said first cylinder.

22. The apparatus of claim 21 wherein said collar means is generally conical.

* * * * *